(12) United States Patent
Li (10) Patent No.: US 6,350,274 B1
(45) Date of Patent: *Feb. 26, 2002

(54) SOFT TISSUE CLOSURE SYSTEMS

(75) Inventor: Shu-Tung Li, Oakland, NJ (US)

(73) Assignee: Regen Biologics, Inc., Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/743,248

(22) Filed: Nov. 5, 1996

Related U.S. Application Data (63) Continuation-in-part of application No. 08/212,008, filed on May 11, 1994, now Pat. No. 5,571,181, which is a continuation-in-part of application No. 07/881,213, filed on May 11, 1992, now Pat. No. 5,326,350.

(51) Int. Cl.[7] .................................................. A61B 17/00
(52) U.S. Cl. ........................ 606/213; 604/168; 604/286
(58) Field of Search ...................... 623/11; 606/213, 606/214, 215, 229, 230, 900; 604/228, 311, 15, 168.01, 286; 128/DIG. 8

(56) References Cited

U.S. PATENT DOCUMENTS

| | | | |
|---|---|---|---|
| 939,693 A | 11/1909 | Holtzmann | 604/60 |
| 3,157,524 A | 11/1964 | Artandi | 106/122 |
| 3,364,200 A | 1/1968 | Ashton et al. | 260/212 |
| 3,506,008 A | 4/1970 | Huck | 604/60 |
| 3,520,402 A | 7/1970 | Nichols | 206/59 |
| 3,742,955 A | 7/1973 | Battista et al. | 128/334 |
| 4,016,877 A | 4/1977 | Cruz, Jr. et al. | 128/156 |
| 4,066,083 A | 1/1978 | Ries | 128/325 |
| 4,215,200 A | 7/1980 | Miyata et al. | 435/273 |
| 4,271,070 A | 6/1981 | Miyata et al. | 260/123 |
| 4,412,947 A | 11/1983 | Cioca | 260/123 |
| 4,421,504 A | 12/1983 | Kline | 604/15 |
| 4,515,637 A | 5/1985 | Cioca | 424/94 |
| 4,578,067 A | 3/1986 | Cruz, Jr. | 604/368 |
| 4,744,364 A | 5/1988 | Kensey | 128/334 R |
| 4,890,612 A | 1/1990 | Kensey | 623/1 |
| 4,891,359 A | 1/1990 | Saferstein et al. | 514/21 |
| 4,970,298 A | 11/1990 | Silver et al. | |
| 5,061,274 A | 10/1991 | Kensey | 606/215 |
| 5,108,421 A | 4/1992 | Fowler | 604/15 |
| 5,129,882 A | 7/1992 | Weldon et al. | 606/213 |
| 5,141,496 A | 8/1992 | Dalto et al. | |
| 5,156,613 A | 10/1992 | Sawyer | 606/213 |
| 5,206,028 A | 4/1993 | Li | 424/484 |
| 5,290,310 A | * 3/1994 | Makower et al. | 128/DIG. 8 |
| 5,308,889 A | 5/1994 | Rhee et al. | 523/113 |
| 5,320,639 A | 6/1994 | Rudnick | 604/15 |
| 5,456,693 A | 10/1995 | Conston et al. | 606/192 |
| 5,676,689 A | * 10/1997 | Kensey et al. | 606/213 |

FOREIGN PATENT DOCUMENTS

| | | |
|---|---|---|
| EP | 0 482 350 A3 | 4/1992 |
| FR | 2265416 | 3/1974 |
| WO | WO 92/01433 | 2/1992 |
| WO | 93/08746 | 5/1993 |

* cited by examiner

*Primary Examiner*—Bruce Snow
(74) *Attorney, Agent, or Firm*—Fish & Richardson P.C.

(57) ABSTRACT

Disclosed is an implant delivery system, e.g., an implant delivery device which includes a detector having a probe positioned at the distal end of a cannula to detect the presence of body fluid flowing in the lumen, and thereby locate the implant member at the wall of the lumen. The implant member further includes a retaining member slidably positioned within the cannula to maintain the implant member at the wall of the lumen when the cannula is withdrawn over the implant member.

22 Claims, 5 Drawing Sheets

SOFT TISSUE CLOSURE SYSTEMS

CROSS REFERENCE TO RELATED APPLICATIONS

This application is a continuation-in-part of U.S. patent application Ser. No. 08/212,008, filed May 11, 1994, now U.S. Pat. No. 5,571,181, which, in turn, is a continuation-in-part of U.S. patent application Ser. No. 07/881,213, filed May 11, 1992, now U.S. Pat. No. 5,326,350.

FIELD OF THE INVENTION

This invention relates generally to the closure and filling of soft tissue sites with self-expandable, bioresorbable, biopolymeric implants, particularly to the closure of percutaneous puncture sites. The present invention is particularly directed to the delivery of such implants with delivery devices which penetrate the soft tissue sites to a defined depth for hemostasis and wound closure. Methods of preparing the implants are also disclosed.

BACKGROUND OF THE INVENTION

It has been routine practice to insert a cannula through a puncture site into a blood vessel for treatment of that vessel, a procedure known in the art as percutaneous transluminal angioplasty. In this procedure, an introducer sheath is inserted into an artery through the puncture site such that a balloon or other type of catheter can then be inserted into the vessel to carry out the procedure within a vessel. One of the complications of this and related procedures is hemorrhaging at the percutaneous puncture site after removal of the catheter and the introducer sheath. In order to stop the bleeding, pressure is applied at the puncture site until hemostasis occurs. Since angioplasty and related procedures often require the use of an anticoagulant, the pressure approach is not always effective and may require a long period of pressurization and occasionally surgical treatment. In some cases, prolonged hospitalization is required.

SUMMARY OF THE INVENTION

The invention relates to the precise delivery of an implant member at an incision extending through tissue and at a lumen wall within a living body to stop the bleeding in post angioplasty and related procedures. The implant member is formed of a material adapted to close the incision (e.g., a self expandable, resorbable, hemostatic and wound closure implant).

In a general aspect of the invention, an implant delivery device includes a detector disposed in fixed relation to a cannula inserted within the incision to detect the presence of body fluid flowing in the lumen, thereby locating the implant member at the wall of the lumen. The implant member further includes a retaining member slidably positioned within the cannula to maintain the implant member at the wall of the lumen when the cannula is withdrawn from the incision.

Preferred embodiments may include one or more of the following features.

The detector includes a tube (e.g., a capillary tube) having a hole disposed near a distal end of the tube to receive fluid from the lumen. The hole conveys the fluid into the tube. The hole is iteratively moved into and out of the lumen, to locate the implant member at the wall of the lumen. In one embodiment, the tube has a sealed distal end and the hole is positioned at the distal end and on the side of the tube to convey fluid through the tube and to a proximal end of the tube disposed external to the living body near a proximal end of the cannula. The proximal end of the tube has an opening through which the conveyed fluid exits. For example, the tube may be made narrow (e.g., a capillary tube). In another embodiment, a pressure monitor is connected to an opening at the proximal end of the tube. In this case, the tube may have a wider dimension than the embodiment in which fluid flows to the proximal end of the tube so that the difference in the pressure of air within the tube can be detected. Moreover, the distal end of the tube need not be sealed but may include the hole at the distal end to detect the systolic pressure of blood flowing in the blood vessel.

In another embodiment, the detector includes a pressure sensor positioned at a distal portion of the cannula. The sensor is moved into and out of the lumen to detect the difference between a pressure within and outside the lumen, thereby locating the implant member at the wall of the lumen.

The retaining member may include an elongated member having a flat plate formed at a distal end of the elongated member and a thumb rest attached at a proximal end of the elongated member.

In another aspect of the invention, the implant delivery device described above is positioned to close an incision at the lumen wall using the following steps. The implant member is placed within the distal portion of the cannula. The cannula is then positioned within the incision to detect the presence of body fluid flowing in the lumen, thereby locating the implant member at the wall of the lumen. The implant member is released from the cannula and maintained at the wall of the lumen by withdrawing the cannula from the incision.

In one embodiment, a retaining member is slidably positioned within the cannula with a distal end of the retaining member contacting a proximal end of the implant member. In use, pressure is applied to the proximal end of the retaining member while simultaneously withdrawing the cannula.

In still another aspect of the invention, a method of positioning an implant member to close an incision extending through tissue and the wall of a lumen within a living body includes the following steps. The implant member is placed within a distal portion of a cannula. A detector is positioned in fixed relation to the cannula. The cannula and the detector are positioned within the incision. The cannula and detector are moved to detect the presence of body fluid flowing in the lumen, thereby locating the implant member at the wall of the lumen. The implant member is then maintained at the wall of the lumen while simultaneously removing the cannula and the detector from the incision.

The implant member is a resorbable, self-expandable tissue and wound closure implant and is generally formed as a dry, compressed porous matrix comprised of biological fibers. As used herein "biological fibers" include natural fibers derived from collagen, elastin, fibrin and polysaccharides as well as bio-synthetic analogs of the natural fibers derived by bioengineering methods such as recombinant DNA methods. In a preferred form of the invention, the matrix is comprised of collagen based fibers of animal or humans.

In particular, the compressed porous matrix of the present invention comprises a matrix having a density from about 0.05 g/cm$^3$ to about 1.0 g/cm$^3$ (preferably, from about 0.1 g/cm$^3$ to about 0.3 g/cm$^3$), and pores of a dimension from about 0.5 µm to about 50 µm (preferably, from about 1 µm to about 10 µm) in a dry state. The pore size is defined as the gap distance of an elongated pore and is measured by the method described in the working example given below or any analogous method. This compressed matrix self expands radially when in contact with an aqueous medium resulting in pores with a dimension of from about 100 μm to about 1,000 μm in its fully expanded configuration, and a corresponding expansion of volume of from about 2 $cm^3/cm^3$ to about 100 $cm^3/cm^3$ (preferably, from about 10 $cm^3/cm^3$ to about 30 $cm^3/cm^3$); and a reduction of density to about 0.01 $g/cm^3$ to 0.10 $g/cm^3$ (preferably, about 0.02 $g/cm^3$ to about 0.06 $g/cm^3$). Preferably, the implant member has a diameter in a range between 1 mm and 6 mm in its compressed state and 5 mm to 50 mm in its fully expanded state, and has a height in a range between 2 mm to 100 mm, which is about the same in either state (e.g., the height in the expanded state is only about 10% or 20% greater than that in the compressed state). The implant member has a relaxation recovery time which ranges from 1 second to 60 seconds (preferably, from 1 second to 20 seconds) can be measured by the method described in the working example given below or any analogous method.

The method for fabricating the resorbable, self-expandable tissue closure implant, in its broadest embodiment, comprises:

a) forming an aqueous dispersion containing biological fibers;
b) pouring the aqueous dispersion into molds;
c) freeze-drying the aqueous dispersion;
d) crosslinking the freeze-dried matrix by treatment with crosslinking agent;
e) spraying the crosslinked matrix with water mist; and then
f) compressing the water mist treated matrix.

The resorbable, self-expandable, soft tissue wound closure implant of the present invention is constructed such that the matrix is highly compressed to provide maximal volume expansion capacity and surface area for fluid absorption, platelet adhesion and hemostasis while maintaining minimal volume for insertion. The highly porous matrix upon expansion also provides maximal surface area for cell infiltration and adhesion for wound healing.

Other features and advantages of this invention will be apparent from the following drawings, detailed description, and claims.

DESCRIPTION OF THE PREFERRED EMBODIMENTS

Figures 1, 1A:
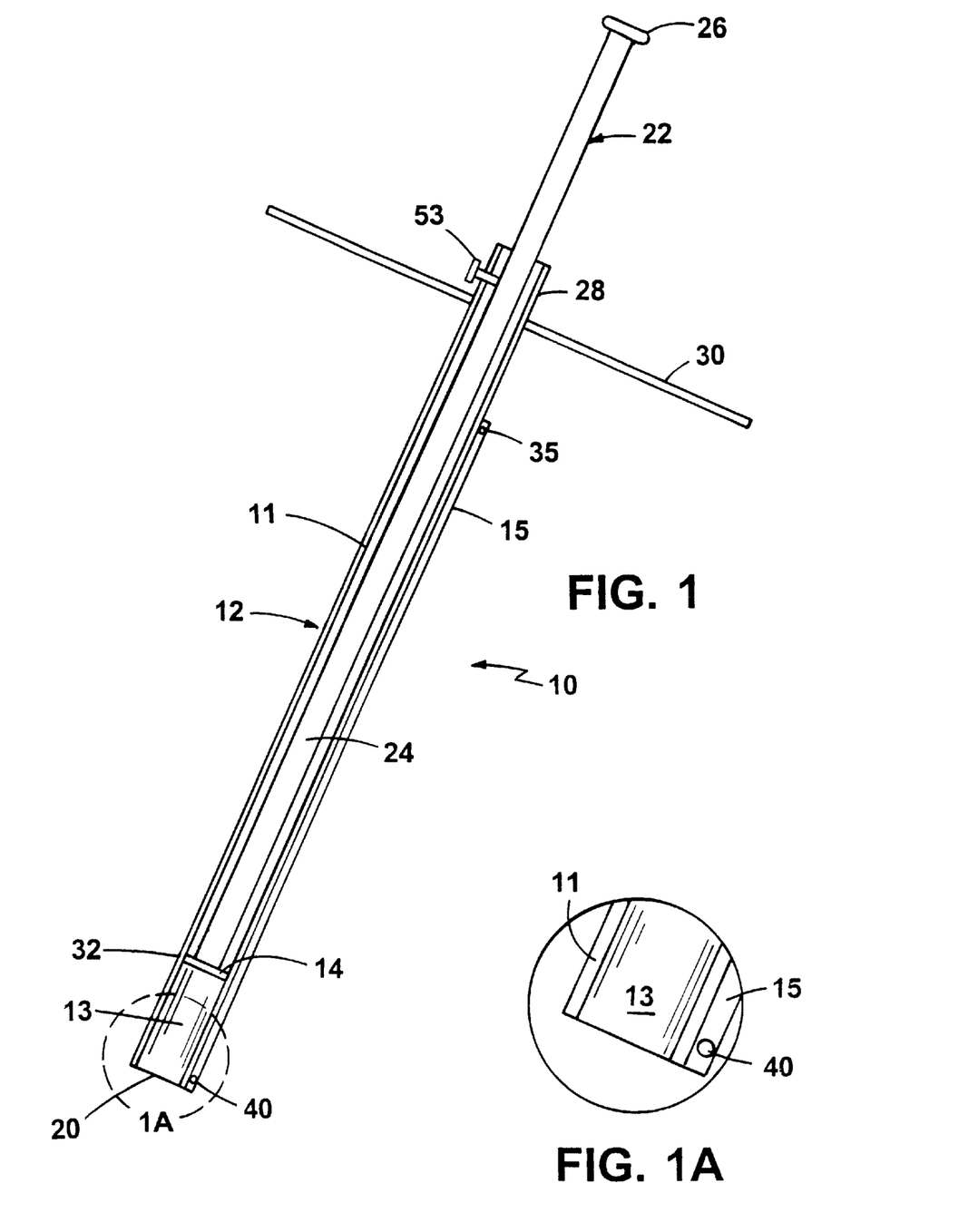
FIG. 1 is a longitudinal cross-sectional view of a soft tissue closure system including an implant delivery device and an implant positioned therein.
FIG. 1A is an enlarged view of the distal end of the implant delivery device and implant of FIG. 1.
Figure 2:
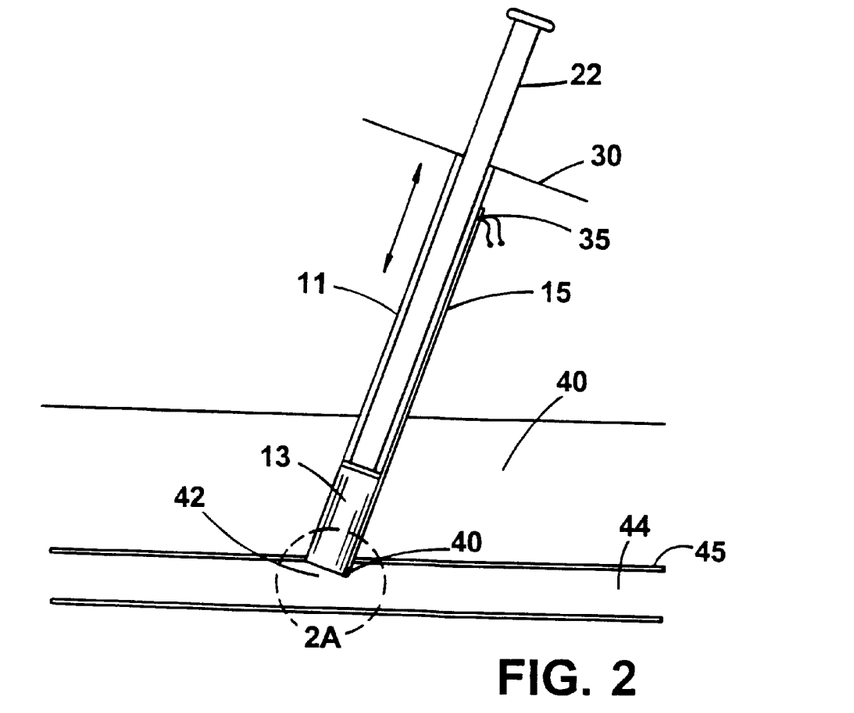
FIGS. 2 and 2A depict the use of the soft tissue closure system at a percutaneous puncture site delivering the implant in cross-sectional view.
Figure 3:
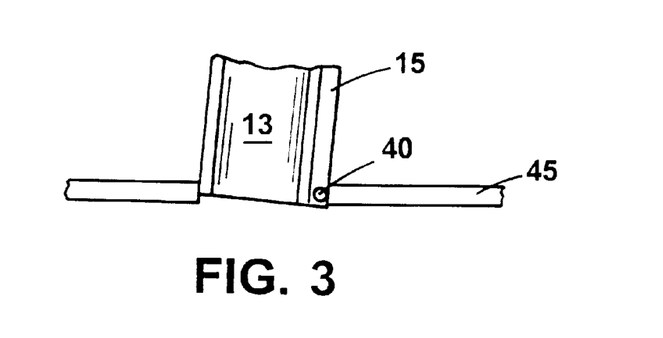
FIG. 3 is an enlarged view of the implant delivery device with the implant properly positioned.

Referring to FIGS. 1–3 wherein like reference numerals refer to the same elements, a soft tissue closure system 10 includes an implant member 13 disposed within an implant delivery device 12. The primary function of delivery device 12 is to deliver implant member 13 at a desired site having an opening. in the soft tissue of a patient and to fill and close the opening.

Referring to FIG. 1, delivery device 12 is made from any biocompatible material including stainless steel; synthetic polymeric materials (e.g., polyethylene, polypropylene, polyvinyl chloride, polystyrene, polytetrafluoroethylene, polyurethane); natural polymers (e.g., collagen, elastin, polysaccharide) and other such biocompatible materials which are well known to those skilled in the art. Preferably, delivery device 12 is made from inexpensive, disposable materials, so that it can be simply discarded after use. For ease of manufacture and disposability, synthetic polymers are preferred.

The implant delivery device includes a cannula 11 having an elongated body extending from an insertable front portion 32 to an outlet 20 at its distal end. Cannula 11 is sized to slidably receive a retaining member 22 which is intproduced at a proximal end 28 of cannula 11.

The retaining member 22 includes an elongated, cylindrical rod-like member 24 having a flat plate 14 attached to its distal end and a thumb rest 26 attached to its proximal end. The flat plate and thumb rest are disposed in planes perpendicular to the longitudinal axis of rod-like member 24. Flat plate 14 has an outside diameter which is slightly less than the inside diameter of insertable portion 32 to enable the rod-like member 24 to slidably move down the longitudinal axis of insertable portion 32 and maintain implant member 13 at outlet 20.

Implant delivery device 12 also includes a narrow tube 15 having a sealed distal end 39 and a side hole 40 at the side of the tube just above outlet 20 of the cannula. side hole 40 serves as a probe for sensing the flow of blood from the artery entering side hole 40. The blood flows to a proximal opening 35 when the insertable front portion 32 is inserted within the puncture site and side hole 40 is extended just beyond the vessel wall. Blood ceases to flow to the proximal opening as soon as the side hole is withdrawn from the blood vessel and is sealed by the vessel wall. The position where blood no longer flows from the proximal opening 35 of the narrow tube 15 defines the depth of insertion of the delivery device. It should be appreciated that delivery device 12 may require rotating so that the plane in which side hole 40 lies faces the direction of blood flow within the vessel.

Cannula 11 is preferably constructed to have an outside diameter which is slightly less than the inner diameter of an introducer sheath typically used in intraluminal procedures to facilitate insertion of the cannula 11 through the skin at the percutaneous puncture site. Depending upon the particular intraluminal procedure, the outside diameter may vary from about 1 mm to about 6 mm. Cannula 11 also includes a flanged projection 30 which is configured to be grasped by the fingers of the user when the implant member 13 is released by retaining member 22 via retraction of the cannula 11. The flanged projection 30 may completely or partially circumscribe tubular body 11 at its proximal end 28.

Implant member 13 is positioned within cannula 11 to be coextensive with outlet 20 at its distal end. Retaining member 22 is slidably introduced within cannula 11 so that its flat plate 14 contacts the proximal end of the implant member. A locking screw 53 at the proximal end of cannula 11 can be used to secure the retaining member 22 with respect to cannula 11.

Figure 2A:
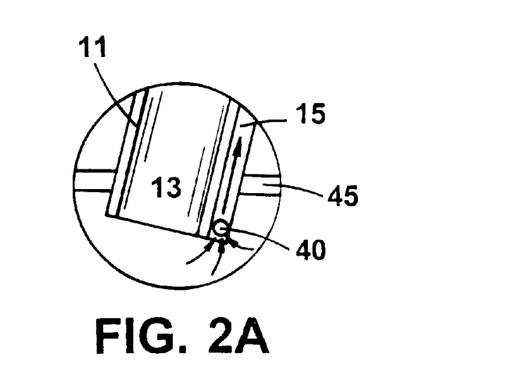

In operation, as shown in FIGS. 2 and 2A, the implant delivery device 12 is slowly introduced within the incision until side hole 40 of narrow tube 15 enters blood vessel 44. Blood flowing through blood vessel 44 enters side hole 40 and flows through narrow tubing 15 to the proximal opening 35, thereby indicating that the puncture site of the vessel has been reached. In most surgical procedures, it is generally preferable that, implant delivery device is introduced using an introducer sheath (not shown). It is important, however, that the introducer sheath should be withdrawn from the vessel, preferably at least one third the distance to the level of the skin.

As shown in FIG. 3, implant delivery device 12 is retracted until the blood stops flowing to proximal opening 35, indicating that side hole 40 has been withdrawn from the blood vessel and is sealed by the vessel wall 45. Note that the diameter of side hole 40 is preferably sized to be approximately that of the thickness of vessel wall 45. To ensure correct positioning, the operator may iteratively move the delivery device back and forth (in the direction of arrows shown in FIG. 2).

Although blood may enter narrow tubing 15 through side hole 40, it will be apparent to the operator that side hole 40 has entered vessel 44 by the sudden outpouring of blood flowing under pressure from vessel to proximal opening 35. Moreover, when an introducer sheath is used in conjunction with implant delivery device 12, the delivery device is generally configured to fit relatively snugly within the sheath so that side hole 40 is sealed by the inner wall of the introducer sheath as it passes therethrough. Further, implant member 13 initially forces the flow of blood within the incision back as delivery device 12 is introduced and implant member 13 begins to absorb blood.

Figure 4:
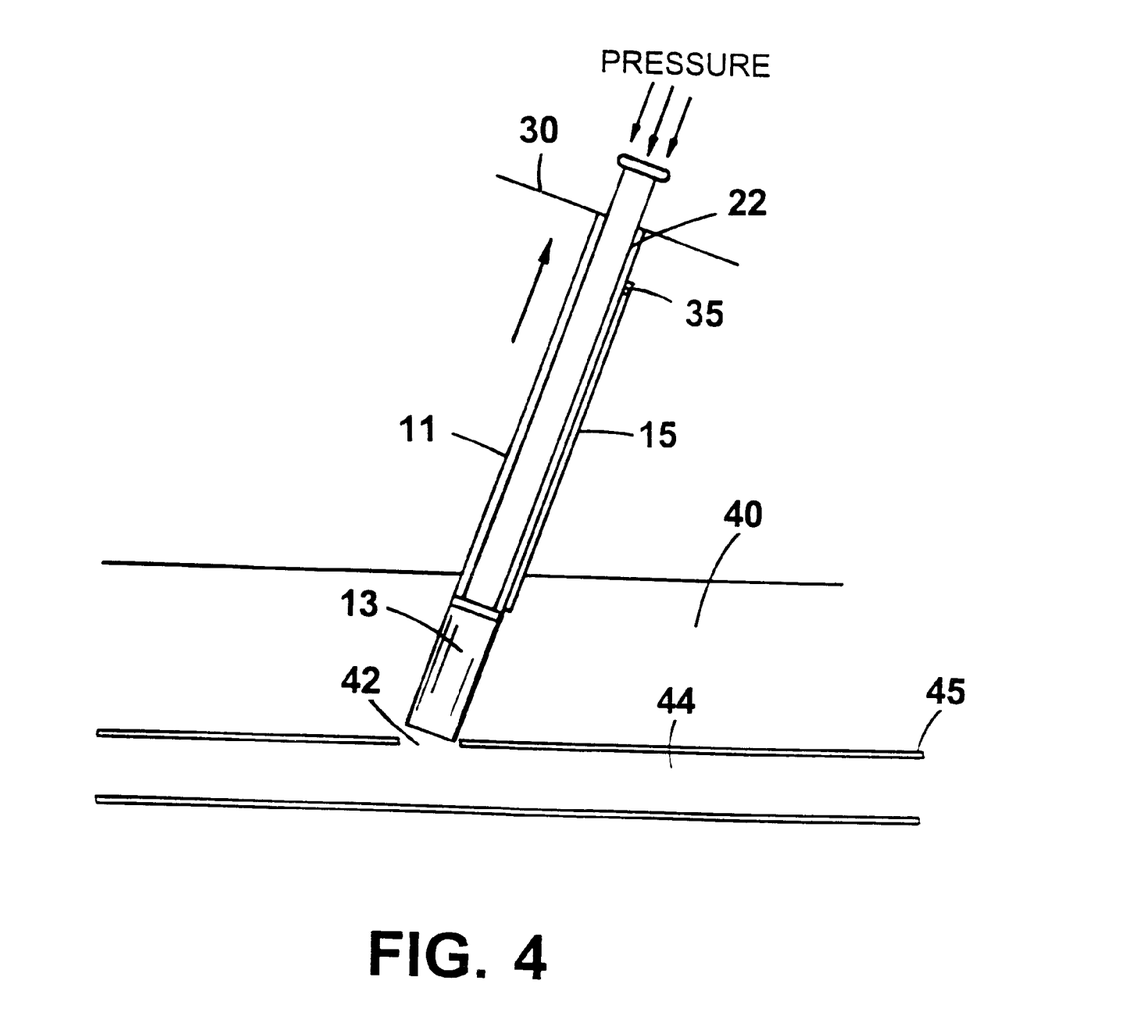
FIG. 4 illustrates the outer tubular member being withdrawn over the implant member.

Referring to FIG. 4, while applying slight axial pressure on retaining member 22 to maintain the position of implant member 13 at the puncture site, cannula 11 is withdrawn over implant member 13 and retaining member 22 until the cannula extends beyond the proximal end of implant member 13. It is important to note that the pressure applied to retaining member 22 need only be sufficient to maintain the position of implant member 13 without advancing its position within blood vessel 44. The tubular and retaining members are then both withdrawn from the incision leaving implant member 13 properly positioned at the vessel wall. The released implant member 13 expands quickly in situ to completely close the puncture site as the delivery device is slowly being removed. Manual pressure is generally required to be applied at the opening of the skin for a period sufficient to allow implant member 13 to swell and close the opening.

Figure 5:
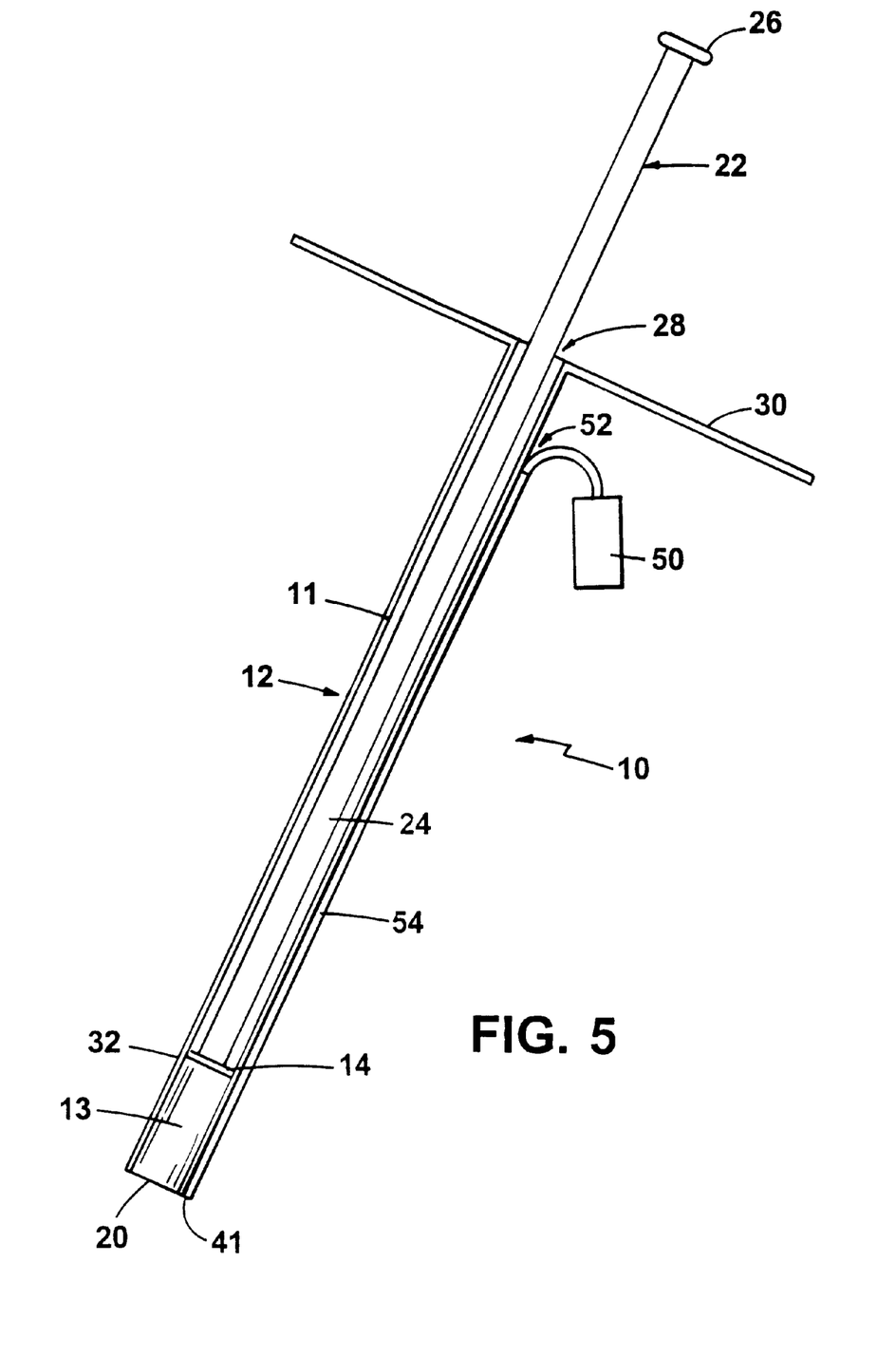
FIG. 5 is an alternative embodiment of the invention.

Other embodiments are within the scope of the claims. For example, referring to FIG. 5, in another embodiment, a pressure monitoring device 50 is connected to the proximal end 52 of tube 54. Pressure monitoring device 50 may be a commercially available monitor, for example, a Minidigital pressure meter, Model DPM200PS, Davis Instrumentation, Baltimore, Md. or simply a sealed tube. The difference in pressure of the air above the blood flowing within tube 52 is detected when a hole 41 is within and outside vessel 44. In other words, the position of the implant with respect to the vessel wall is determined through the pressure monitor readings which indicate pulsation of the blood within the sealed tube. When tube 52 is moved from within vessel 44 to just outside the vessel wall, the pressure changes from a systolic pressure reading to a damped pressure reading or from pulsation of no blood to a damping of the blood in the sealed tube. Note that unlike the embodiment discussed above in conjunction with FIGS. 1–4, tube 54 need not have a narrow dimension since the blood does not flow to proximal end 52. Rather, as shown in FIG. 5, tube 54 can have a wider dimension or other geometry so long as the proximal end is connected to a pressure monitor or a sealed tube. Note also, that the hole at the distal end of tube 54 may either be positioned at the distal end of the tube or along the side of the tube. As shown in FIG. 5, hole 41 is positioned at the distal end of tube 54 (i.e., the distal end need not be sealed). Hole 41 in this position is still capable of detecting pulsation of the blood within the blood vessel.

Figures 6, 6A:
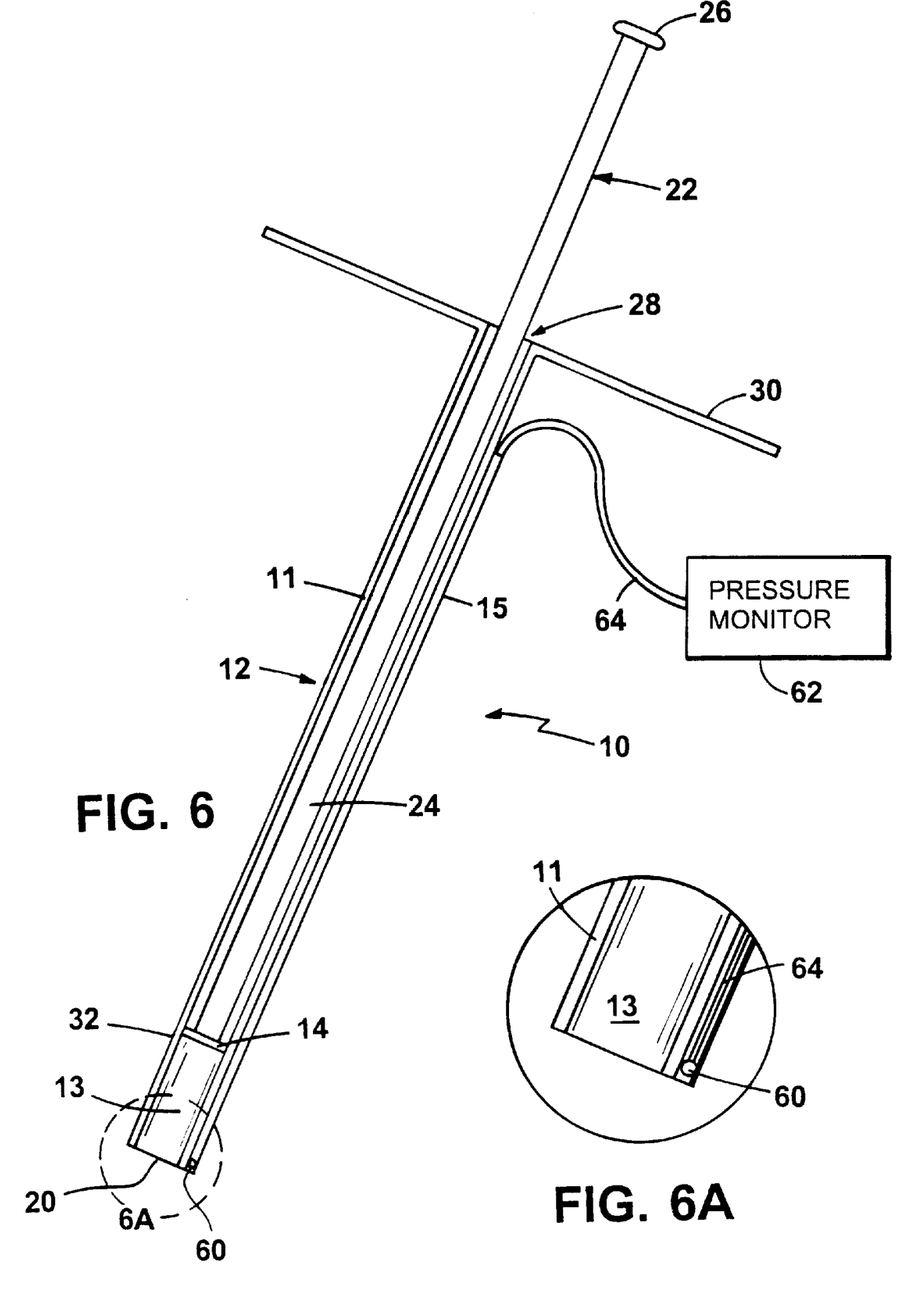
FIG. 6 is still another alternative embodiment of the invention.
FIG. 6A is an enlarged view of the distal end of the embodiment of FIG. 6.

In another embodiment, shown in FIGS. 6 and 6A, the probe may be in the form of a pressure sensor 60 which is positioned at the distal end of cannula 11 to directly detect the difference in pressure within and outside the blood vessel. In this embodiment, pressure sensor 60 is connected to pressure monitoring equipment 62 via wires 64, and may be in the form of a commercially available mini-mechanical, mini-electronic or electromechanical pressure sensing device.

In the above described embodiments, the soft tissue closure system was used to close a percutaneous puncture in an artery. However, it should be understood from the above discussion that the present invention is applicable to openings in other ducts or lumens. Such openings may be the result of surgical procedures including those related to filling openings after removal of malignant tumors, necrotic tissues, degenerative tissues, deep bullet wounds, knife stabbings, and the like openings created by plastic or cosmetic surgery, and the like, can also be filled using the closure system 10. Still further, closure system 10 may be used to stop the bleeding and fill openings created during tissue biopsy applications where a biopsies needle or other biopsy device is used.

Implant member 13 is made primarily from biopolymers, such as proteins, polysaccharides or the like. Preferably, a collagen based material is used due to its intrinsic hemostatic properties.

Type I to type XIX collagens may be used either singularly or in combination for the manufacture of the implantable member 13. Preferably, type I collagen is used due to the availability of this material in large quantity, the ease of its isolation and purification, and proven hemostatic properties. The primary source of type I collagen is tendon, skin, bone, and ligament. Both human and animal tissues may be used to isolate the collagen. In general, animal tissues are preferred due to easy availability in fresh forms from local slaughter houses.

In preparing the implantable member 13, type I collagen is first isolated and purified. A review of the preparation of collagen can be found in "Methods in Enzymology," vol. 82, pp. 33–64, 1982. In particular the collagen of the present invention may be prepared by the following method.

First, a native source of type I collagen, such as skin, tendon, ligament or bone is first cleaned of fat, fascia and other extraneous matter and washed. The clean and washed collagen containing material is then comminuted by slicing or grinding. Bone material is subsequently subjected to a demineralization procedure. This is achieved either with an acid solution such as hydrochloric acid or a solution of chelating agent such as ethylenediaminetetra-acetic acid.

The material is then subjected to a defatting treatment using fat solubilizing agents such as ethanol, propanols, ethers or a mixture of ether and alcohol. The defatted collagen containing material is then extracted in a neutral salt solution to remove neutral salt soluble material.

Typically, 1 M NaCl solution is used for this purpose. The high ionic strength salt solution weakens the non-specifically bound non-collagenous materials which are solubilized and removed. The salt extracted collagen containing material is then washed with deionized, distilled water.

The neutral salt extracted collagen containing material is then subjected to an acid extraction in the presence of a structure stabilizing salt to further remove acid soluble non-collagenous materials. Applicable acids include acetic acid, lactic acid, hydrochloric acid, sulfuric acid, phosphoric acid, and the like. Regardless of which acid is used, the pH of the acid solution is adjusted to be below 3. The salt used include sodium chloride, ammonium sulfate, sodium sulfate, or the like. Acid extraction weakens the interaction between the collagen and the acidic non-collagenous impurities which are solubilized and removed.

The acid extracted collagen is then neutralized by adjusting the pH to its isoelectric point at pH of from about 6 to about 7 by adding a base. Applicable bases include sodium hydroxide, potassium hydroxide, ammonium hydroxide, and the like. By adding a base, the collagen coacervates. The coacervated collagen is then filtered by means well known in the art such as using a stainless steel mesh filter under vacuum.

The acid extracted, base neutralized collagen is then washed with deionized, distilled water to remove the residual salt formed by the neutralization procedure. The washed collagen is then subjected to a base extraction in the presence of a structure stabilizing salt. Such bases are well known in the art such as sodium hydroxide, potassium hydroxide, calcium hydroxide and the like. Regardless of which base is used, the pH of the solution is adjusted to be above 13. Base extraction weakens the interaction between collagen and the basic non-collagenous impurities. By adding the base, non-collagenous materials are solubilized and removed. The base also lowers the isoelectric point due to a partial deamidation of glutamines and asparagines in collagen which produce additional carboxyl groups. The base extracted collagen is then coacervated by adjusting the pH to its isoelectric point at a pH of from about 4.5 to 5.5 by adding an acid to the collagen dispersion so as to fully separate the fibers from the solution for ease of filtration. Such acids include hydrochloric acid, sulfuric acid, acetic acid, lactic acid, phosphoric acid and the like. The coacervated collagen is then filtered. After discarding the extraction solution, the fibers are washed with deionized, distilled water to remove the residual salts resulting from neutralization of the extraction solutions. The thusly purified collagen is stored in a freezer or stored in freeze-dried form for the preparation of collagen implantable member 13.

To fabricate a collagen implantable member 13, a collagen dispersion is first prepared in a manner well known in the art. One such preparation is taught in U.S. Pat. No. 3,157,524. Another preparation of collagen dispersion is taught in U.S. Pat. No. 3,520,402.

In particular, the collagen dispersion of the present invention may be prepared by the following method.

The purified collagen material is first dispersed in $1 \times 10^{-4}$ M NaOH solution to swell the collagen fibers. The collagen material is then homogenized by any conventional means such as with a blender or homogenizer so as to fully disperse the fibers. The homogenized collagen is then filtered to remove any unswollen aggregates by means well known in the art such as by passing the dispersion through a stainless steel mesh screen. The pH of the dispersion is adjusted to about 7.4 by adding 0.01 M HCl. The initial dispersion in a base allows the neutralization step to be carried out without passing the isoelectric point so as to not cause coacervation of the collagen and obtain a more uniform dispersion at pH 7.4. The dispersion is then desired by vacuum. The resulting collagen dispersion may then be used to prepare the self-expandable implant device for closure of soft tissue.

Typically, the weight percent of collagen in a dispersion is from about 0.5 to about 5.0, preferably in the range from about 0.75 to about 2.0. Higher weight percent of collagen than 5.0 in the dispersion can be obtained by centrifuging the dispersion in a centrifuge and discard the supernatant. Generally, the higher the centrifugal force applied to the dispersion, the higher the weight percent of collagen in the dispersion after removing the supernatant.

In one embodiment of the present invention, if the collagen soft tissue closure system is intended to function as a medicinal delivery vehicle, then in addition to the type I collagen, medicinal additives may optionally be included in the dispersion, such as antibiotics, thrombin, polysaccharides such as hyaluronic acid, chondroitin sulfates, alginic acids, chitosan and the like, growth factors such as epidermal growth factors, transforming growth factor beta (TGF-β) and the like, glycoproteins such as fibronectin, laminin, and the like, type II through type XIX collagens, and mixtures thereof.

The collagen dispersion is then poured into molds. The shape of the mold may be cylindrical, rectangular, spherical or any other shape. The size and shape of the mold may be designed to obtained the optimal material for further processing. Preferably, a cylindrical-shaped mold is used to close a puncture wound site. The size of the mold is larger than the inner diameter of insertable front portion 32. For example, for a 2 mm internal diameter (I.D.) insertable front portion 32, and a cylindrical implantable collagen member 13, the diameter of the mold is preferably in the range of from about 3 mm to about 15 mm and the height of the mold is from about 5 mm to about 25 mm.

The molds containing the dispersion are then placed in a freezer maintained at a temperature of from about −10° C. to about −50° C. for a length of time sufficient to freeze the water present in the dispersion, generally for about 1 to about 24 hours. The frozen dispersion is then subjected to freeze-drying so as to remove the frozen water. This freeze-drying procedure is carried out in a commercial freeze dryer, such as that manufactured by Virtis, Stokes or Hull, at conditions well known to those skilled in the art. Typically, the vacuum within the drying chamber is maintained at from about 50 mm to about 300 mm of Hg, at a temperature of from about −10° C. to about −50° C. for about 16 to about 96 hours. The temperature is then raised to about 25° C. for about 3 to 24 hours.

The freeze-dried, highly porous collagen matrix is then subjected to a crosslinking process to introduce additional intermolecular crosslinks to stabilize the form of the collagen matrix. The crosslinking is carried out by means well known in the art. Any reagents which can chemically react with amino groups, hydroxyl groups, guanidino groups, carboxyl groups that can link the side chains of different collagen molecules may be used to crosslink the collagen matrix. This can be accomplished with chromium sulfate, formaldehyde, glutaraldehyde, carbodiimide, adipyl chloride, hexamethylene diisocyanate and the like. The rate of in vivo resorption of the collagen is dependent upon the degree of intermolecular crosslinking in the collagen matrix. Factors controlling the extent of crosslinking are the type and concentration of the crosslinking agent; the pH, time and the temperature of incubation in the liquid phase; or the vapor pressure of the crosslinking agent, time, temperature and the relative humidity when carrying out crosslinking in the vapor phase. Desirably, the collagen matrix of the present invention is crosslinked to the extent that the collagen is completely resorbed within about 2 to about 10 weeks.

Appropriate crosslinking of the freeze-dried matrix introduces several very important properties of the present invention for the specified medical applications as a soft tissue closure device.

For example, effective crosslinking locks in the physical geometry of the matrix which is defined by the shape of the mold. Consequently, the matrix behaves elastically when a stress is applied to the matrix. That is, when the matrix is later compressed physically, it will return to its original form and size upon relaxation or release of the external stress, or expand to the extent to conform to a physical barrier such as the puncture wall. This elastic behavior of the appropriately crosslinked freeze-dried collagen matrix is especially manifested when the collagen matrix is in the wet state, as when it absorbs blood at the puncture site. This is a result of hydrophilicity and the Donnan osmotic pressure of the collagen matrix. The recovery time from the compressed state to the original shape in the wet state is as short as from about 1 second to about 60 seconds. Desirably, the recovery time is from about 1 to about 20 seconds.

Another important property resulting from crosslinking the collagen matrix is its volume expansion capacity from the compressed state to the expanded state. The volume expansion capacity of the crosslinked collagen matrix of the present invention is limited by the size of the mold which defines the total volume of the matrix of the present invention. The total volume of a matrix is defined by the geometry of the mold. Typically, when the mold is of the form of a cylinder, the volume is defined by the area of the base of the cylinder and the height of the cylinder. The desirable volume of the matrix when in use for puncture site closure is dependent upon the particular size of the introducer sheath used. As an example, when a 9F (about 3 mm) introducer sheath is used, the desirable dimension of a cylindrical matrix is to have a base dimension of from about 6 mm to about 15 mm, and a height of from about 5 mm to about 25 mm. This means that the volume of the compressed matrix will expand about 3 to 20 times upon delivery and self expansion.

Yet an additional property which can be controlled by crosslinking the collagen matrix is its density. Dependent upon the particular puncture site to be repaired and the physical, chemical and biological requirements, the density of the compressed matrix is in the range of from about 0.05 g/cm$^3$ to about 1.0 g/cm$^3$, and the density of the matrix in the fully expanded configuration may vary from about 0.01 g/cm$^3$. Typically, to close a puncture site from angioplasty or related procedures, the density of the matrix in the compressed state various from about 0.1 g/cm$^3$ to about 0.3 g/cm$^3$ and in the fully expanded configuration various from about 0.02 g/cm$^3$ to about 0.06 g/cm$^3$.

Another property resulting from crosslinking collagen matrix is the pore structure of the crosslinked matrix. The fully expanded crosslinked collagen matrix has a pore size from about 100 $\mu$m to about 1,000 $\mu$m. The pore size is drastically reduced in the compressed state to a value of from about 0.5 $\mu$m to about 50 $\mu$m. The compression of the crosslinked matrix permits the matrix to be inserted into a small volume for delivery and the subsequent self expansion of the matrix upon delivery allows the matrix to expand to the extent to conform to the puncture hole.

The degree of crosslinking of the collagen matrix of the present invention can be measured by the hydrothermal shrinkage temperature ($T_s$) of the matrix, i.e. the onset temperature at which the matrix begins to shrink in its dimension in an aqueous environment as a result of the unwinding of the triple helical structure of the collagen molecules. The methods for measuring the shrinkage temperature of a material is well known in the art, such as by a differential scanning calorimeter, or by measuring the dimensional change using a cathetometer. Generally, the degree of crosslinking is such that the shrinkage temperature of the collagen matrix is in the range of from about 50° C. to about 75° C., preferably from about 55° C. to about 65° C.

As an example, the collagen matrix can be crosslinked with formaldehyde vapor. Either commercial formaldehyde vapor, or vapor of formaldehyde generated from a formaldehyde solution may be used. Particularly, the crosslinking can be conducted in a chamber with a relative humidity in the range of from about 80% to about 100%, preferably in the range from about 85% to about 95%, and in the presence of an excess amount of formaldehyde vapor, at a temperature of about 25° C. for a period from about 30 minutes to about 8 hours. Specifically, crosslinking by formaldehyde vapor generated from 1% formaldehyde solution at 25° C. and at 95% humidity for 60 minutes produces a collagen matrix of a shrinkage temperature of from about 55° C. to about 65° C. for a matrix of density from about 0.02 g/cm$^3$ to about 0.1 g/cm$^3$ in the fully expanded configuration.

The crosslinked collagen matrix can then be subjected to a water mist treatment. Any commercial water mist sprayer is suitable for this purpose. As an example, the collagen matrices can be sprayed for about 10 seconds to about 60 seconds while the collagen matrices are being tumbled in a container at about 25° C. The water mist treated matrices are then equilibrated in a closed container for about 30 minutes to further soften the matrices for the compression step which follows. As a result of this water treatment, the collagen matrices have a water uptake of about 10 to 40% by weight, based on the weight of the dry material. The water mist treated collagen matrix is then subjected to mechanical compression to reduce its size in order to fit into insertable portion 32.

Particularly, when the matrix is in a cylindrical form, the mechanical compression is applied in the radial direction such that the base area is reduced to approximately the size of the I.D. of insertable portion 32. Generally, the compressed collagen matrix has a volume of from about ¹⁄₁₀₀ to ½ of the non-compressed matrix. The compressed collagen implantable member 13 is then inserted into insertable front portion 32. At this point, the loaded soft tissue closure system is individually packaged for sterilization.

The crosslinking of the matrix, the water mist treatment and the mechanical compression are important aspects of the present invention. More importantly, the sequence of operation as described in this invention is critical in providing the desirable properties of the collagen matrix. The density, the pore structure and the extent of volume expansion of the compressed collagen implant member are directly related to how the collagen matrix material is made. For example, a change of the order from the present invention to water mist treatment, mechanical compression and then crosslinking the matrix will result in a matrix which will not self-expand when the stress is released and which does not have the blood absorption capability.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever. All publications, including U.S. patents, cited herein are incorporated by reference.

Preparation of a Collagen Dispersion

The fat and fascia of the bovine flexor tendon are carefully cleaned and removed and washed with water. The cleaned tendon is frozen and diminuted by slicing into 0.5 mm slices with a meat slicer. The tendon is first defatted with isopropanol (tendon:isopropanol=1:5 v:v) for 8 hours at 25° C. under constant agitation. The extraction solution is discarded and equal volume of isopropanol is added and the tendon slices is extracted overnight at 25° C. under agitation. The tendon is then extensively washed with deionized, distilled water to remove the residual isopropanol. The defatted tendon is then extracted with 10 volumes of 1 M NaCl for 24 hours at 4° C. under agitation. The salt extracted tendon is washed with deionized, distilled water. The fibers are next extracted with 10 volumes of 1.0 M NaOH for 24 hours at 25° C. in the presence of 1 M $Na_2SO_4$ under constant agitation. The alkaline extracted collagen is then collected by filtration and neutralized with 0.1 M HCl and the fibers collected, washed to remove the residual salt and frozen.

An aliquot of the above purified fibers is first suspended in $1 \times 10^{-4}$ M NaOH solution. The amount of fibers and base solution used is such that a 1.5% (w/v) of collagen suspension is reached. The swollen fibers are then homogenized in a stainless steel blender for 60 seconds. The thusly dispersed collagen material is filtered through a 40 mm stainless steel mesh. The pH of the dispersion is then adjusted to about 7.4 by adding 0.01 M HCl. The dispersed material is then de-aired by vacuum and stored at 4° C. until use.

Preparation of a Collagen Soft Tissue Closure Implant

A collagen dispersion prepared in a manner described above is poured into stainless steel molds of 15 mm in diameter and 10 mm in height. The collagen containing molds are then subjected to a freeze-drying procedure using a Virtis commercial freeze dryer. The conditions for freeze-drying are: freeze at −40° C. for 6 hours, drying at 150 µm Hg at −10° C. for 24 hours followed by drying at 25° C. for 8 hours. The freeze-dried collagen matrices are then subjected to a formaldehyde vapor crosslinking in a crosslinking chamber containing excess amount of formaldehyde vapor (generated by a 1% formaldehyde solution at 25° C.), 95% relative humidity at 25° C. for 60 minutes. The crosslinked collagen matrices are sprayed with water mist for 10 seconds and equilibrated in a closed container for an additional 30 minutes. The water mist treated matrices are then compressed by rotating between two soft plastic plates with a gap of 2.5 mm such that the diameter of the 15 mm sponge matrix reduces to about 2.5 mm. The compressed collagen matrix is then inserted into a pre-fabricated implant delivery means of 2.5 mm I.D. and 3.0 mm O.D. (member 11, FIG. 1).

Preparation of a Collagen Soft Tissue Closure Implant which Contains Thrombin

A collagen dispersion is mixed uniformly with thrombin (collagen:thrombin=10:1 w/w). The thoroughly mixed collagen/thrombin gel is then poured into the stainless steel molds in the above-described manner. The subsequent steps are also identical to those described above.

Preparation of a Polysaccharide Soft Tissue Closure Implant

Chitosan (Sigma Chemicals, St. Louis, Mo.) is dissolved in 1% acetic acid. The amount of chitosan and acid solution used is such that a 1.5% of chitosan solution is reached. An aliquot of the chitosan solution is slowly neutralized by adding 0.01 M NaOH to pH 6. The solution thus prepared is poured into stainless steel molds and processed as described above.

Characterization of Collagen Soft Tissue Closure Implant a) Density ($g/cm^3$)

The apparent density of the soft tissue closure implant in the compressed and fully expanded configuration is determined by first weighing the collagen matrix to obtain the dry weight. The volume of the matrix is then determined from the radius and the height of the sponge according to: $V = \pi \times r^2 \times h$, where r is the radius and h is the height of the matrix. The density of the collagen soft tissue closure implant of the present invention is in the range of from about 0.10 $g/cm^3$ to about 1.0 $g/cm^3$ for the compressed matrix, and is from about 0.01 $g/cm^3$ to about 0.1 $g/cm^3$ for the fully expanded matrix.

b) Volume Expansion Capacity (v/v)

The volume expansion capacity is defined as the expansion of the volume of the matrix per unit volume of the soft tissue closure device. The volume of the compressed collagen matrix is first determined by measuring the dimensions of the matrix. The collagen matrix is next immersed in a buffered solution at pH 7.4 at 25° C. for 5 minutes. The volume of the expanded wet matrix is then determined. The volume expansion capacity (v/v) of the collagen matrix is calculated as the volume of the expanded matrix divided by the volume of the compressed matrix. The volume expansion capacity of the collagen soft tissue closure implant of the present invention is in the range of from about 2 $cm^3/cm^3$ to about 100 $cm^3/cm^3$.

c) Pore Size (µm)

The pore size is obtained from the scanning electron micrographs (SEM) of cross-sections of the collagen implant in its compressed and fully expanded configurations. The pore size of the compressed matrix is defined as the gap distance of a compressed elongated pore. The pore size of the expanded matrix is defined as the average of the longest distance and the shortest distance of an open pore. The pore size of the collagen matrix of the present invention is in the range of from about 0.5 µm to about 50 µm for the compressed implant, and is from about 100 µm to about 1,000 µm for the fully expanded implant.

d) Relaxation Recovery Time (Seconds)

The collagen soft tissue closure implant of the present invention in its compressed configuration is pushed out from the disposable delivery means into a buffered solution, pH 7.4 at 25° C. The compressed matrix is relaxed, hydrated and self expanded to the fully expanded configuration. The time it takes to recover to the fully expanded configuration is recorded. The relaxation recovery time for the present invention is in the range of from about 1 second to about 60 seconds.

e) Shrinkage Temperature (° C.)

A 10 mg sample of the collagen matrix is first wetted in a buffered solution, pH 7.4. The sample is sealed into an aluminum sample pen and inserted into a sample holder of a differential scanning calorimeter. The buffer solution is used as a reference. The heating rate is 50° C./min. The shrinkage temperature is defined as the onset of the endothermic peak from the heat capacity versus temperature plot. The thermal shrinkage temperature of the collagen soft tissue closure implant of the present invention is in the range of from about 50° C. to about 75° C.

Use of a Collagen Soft Tissue Closure Implant (with a Sheath)

An appropriately sized collagen soft tissue closure implant is inserted into a puncture site with the introducer sheath partially removed. The collagen implant is released into the puncture site and allowed to be fully hydrated and self-expanded in situ for 5 minutes. The above procedure is performed in a manner described above. The delivery means is then slowly withdrawn, and slight pressure applied to the wound for 2 to 5 minutes to ensure complete hemostasis and wound closure.

Use of a Collagen Soft Tissue Closure Implant (without a Sheath)

An appropriately sized delivery means containing a collagen implant is inserted through a percutaneous site to the tissue site of interest. The collagen implant is then released out of the tubular delivery means in a manner described above. The collagen implant self expands to fill the voids of the soft tissue site.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An implant delivery device for delivering an implant member to an incision at a wall of a lumen within a living body, said implant delivery device comprising:
    a cannula extending along an axial direction and having a distal portion to be introduced into the incision, the distal portion configured to suppress movement of the implant member relative to the cannula in a radial direction orthogonal to the axial direction;
    a retaining member slidably positioned within the cannula for maintaining the implant member at the distal portion of the cannula during delivery of the implant member at the incision at the wall of the lumen, the retaining member including a solid plate disposed at a distal end thereof for engaging the implant member; and
    a detector fixedly attached to the cannula for detecting the body fluid flowing in the lumen and thereby locating the implant member at the wall of the lumen, the implant member being simultaneously releasable and maintained at the wall of the lumen by withdrawal of the cannula from the incision.

2. The implant delivery device of claim 1, wherein the detector includes a wall forming a tube, the tube having
    a proximal end to be disposed external to the living body, and
    a distal end to be inserted into the living body,
    the wall forming an entry hole for enabling fluid from the lumen to enter the tube, the entry hole being formed proximate to the distal end of the tube.

3. The implant delivery device of claim 2, wherein
    the distal end of the tube is sealed; and
    the tube is configured to convey the fluid toward the proximal end of the tube.

4. The implant delivery device of claim 3, wherein the wall forming a tube forms an exit hole for enabling fluid to exit the tube, the exit hole being formed proximate to the proximal end of the tube.

5. The implant delivery device of claim 2,
    wherein the wall forming a tube forms an exit hole for enabling fluid to exit the tube, the exit hole being formed proximate to the proximal end of the tube, and
    wherein the detector further includes a pressure monitor connected to the exit hole.

6. The implant delivery device of claim 5, wherein the pressure monitor is configured to detect a pressure of air within the tube.

7. The implant delivery device of claim 1, wherein the detector includes a pressure sensor positioned at a distal portion of the cannula.

8. The implant delivery device of claim 1, wherein the implant member is a compressed bioresorbable implant member disposed within the distal portion of the cannula, the implant member being radially expandable, when wetted, from a compressed state to an uncompressed state, and having, in its compressed state,
    a volume expansion rate ranging from 2 cm$^3$/cm$^3$ to 100 cm$^3$/cm$^3$,
    a pore size ranging from 0.5 $\mu$m to 50 $\mu$m, and
    a density ranging from 0.05 g/cm$^3$ to 1 g/cm$^3$;
and having, in its uncompressed state,
    a pore size ranging from 100 $\mu$m to 1,000 $\mu$m,
    a density ranging from 0.01 g/cm$^3$ to 0.1 g/cm$^3$, and
    a relaxation recovery time ranging from 1 second to 60 seconds.

9. The implant delivery device of claim 8, wherein, in its compressed state, the implant member has
    a volume expansion rate ranging from 10 cm$^3$/cm$^3$ to 30 cm$^3$/cm$^3$,
    a pore size ranging from 1 $\mu$m to 10 $\mu$m, and
    a density ranging from 0.1 g/cm$^3$ to 0.3 g/cm$^3$;
and in its uncompressed state, the implant member has
    a pore size ranging from 200 $\mu$m to 400 $\mu$m,
    a density ranging from 0.02 g/cm$^3$ to 0.06 g/cm$^3$, and
    a relaxation recovery time ranging from 1 second to 20 seconds.

10. The implant delivery device of claim 9, wherein the implant member is made of a biocompatible and biopolymeric material.

11. The implant delivery device of claim 10, wherein the biocompatible and biopolymeric material is collagen.

12. The implant delivery device of claim 8, wherein the implant member is made of a biocompatible and biopolymeric material.

13. The implant delivery device of claim 12, wherein the biocompatible and biopolymeric material is collagen.

14. The implant delivery device of claim 1, wherein the distal portion of the cannula is sized so that the implant member is held in the distal portion by tension.

15. The implant delivery device of claim 14, wherein the distal portion of the cannula has an inner diameter that is smaller than a diameter of the implant member.

16. A method of closing an incision in a wall of a lumen, said method comprising:
    engaging an implant member within a distal portion of a cannula;
    positioning the distal portion of the cannula within the incision;
    moving a detector fixedly attached to the cannula to detect the presence of body fluid flowing in the lumen, thereby locating the implant member at the wall of the lumen; and maintaining the implant member at the wall of the lumen by applying a pressure to a proximal end of a retaining member having a solid plate engaging the implant member, and while the pressure is thus applied to the proximal end of the retaining member, removing the distal portion of the cannula from the incision.

17. The method of claim 16, wherein moving the detector includes providing a wall forming a tube having a sealed distal end and an entry hole through the wall near the sealed distal end for enabling body fluid from the lumen enter the tube, and iteratively moving the entry hole into and out of the lumen to locate the implant member at the wall of the lumen.

18. The method of claim 17, wherein moving the entry hole into the lumen causes the body fluid to be conveyed through the tube to an opening at a proximal end of the tube external to the living body.

19. The method of claim 16, wherein moving the detector includes iteratively moving a pressure sensor into and out of the lumen, and monitoring the difference between a pressure within the lumen and a pressure outside the lumen, thereby locating the implant member at the wall of the lumen.

20. The method of claim 16, wherein moving the detector includes providing a pressure sensor at the distal Portion of the cannula, iteratively moving the pressure sensor into and out of the lumen, and monitoring the difference between a pressure within the lumen and a pressure external to the lumen, thereby locating the implant member at the wall of the lumen.

21. The method of claim 16, wherein maintaining the implant member at the wall of the lumen includes slidably positioning a retaining member within the cannula, with a distal end of the retaining member contacting a proximal end of the implant member during removal of the cannula.

22. A method of closing an incision extending through a wall of a lumen within a living body, said method comprising:

providing an implant delivery device having
a cannula extending in an axial direction and having a distal portion for insertion into the incision, and
a detector fixedly attached to the cannula for detecting body fluid flowing in the lumen;

placing an implant member on a flat plate within the distal portion of the cannula;

positioning the implant delivery device within the incision;

moving the implant delivery device to detect the presence of body fluid flowing in the lumen, thereby locating the implant member at the wall of the lumen; and maintaining the implant member at the wall of the lumen while simultaneously removing the implant delivery device from the incision.

* * * * *